United States Patent
McCullough et al.

(10) Patent No.: US 9,089,140 B2
(45) Date of Patent: Jul. 28, 2015

(54) CLEANING AND SANITIZING FILM

(75) Inventors: Mike McCullough, Franklin, IN (US); Tony McCullough, Bargersville, IN (US); Charlie Martin, Lexington, KY (US)

(73) Assignee: Sanikleen, LLC, Franklin, IN (US)

( * ) Notice: Subject to any disclaimer, the term of this patent is extended or adjusted under 35 U.S.C. 154(b) by 0 days.

(21) Appl. No.: 13/403,148

(22) Filed: Feb. 23, 2012

(65) Prior Publication Data

US 2012/0213865 A1    Aug. 23, 2012

Related U.S. Application Data

(60) Provisional application No. 61/445,586, filed on Feb. 23, 2011.

(51) Int. Cl.
*A01N 59/16* (2006.01)
*A01N 59/20* (2006.01)
*A01N 59/00* (2006.01)
*A01N 59/14* (2006.01)

(52) U.S. Cl.
CPC ............. *A01N 59/20* (2013.01); *A01N 59/00* (2013.01); *A01N 59/14* (2013.01)

(58) Field of Classification Search
CPC ....... A01N 59/00; A01N 59/14; A01N 59/20; A01N 25/02; A01N 59/16; A01N 2300/00; A01N 59/01

USPC .......................................... 424/618, 637, 638
See application file for complete search history.

(56) References Cited

U.S. PATENT DOCUMENTS 3,992,146 A * 11/1976 Fazzalari .................... 422/29
4,461,721 A * 7/1984 Goettsche et al. ............ 252/607
2007/0270612 A1* 11/2007 Pompeo et al. ............... 564/123

FOREIGN PATENT DOCUMENTS

EP          0039538 A1 *  3/1981

OTHER PUBLICATIONS

Mao et al., Bulletin of Insectology, 64 (1);69-72, 2011.*
Watanabe et al., J. Mat. Sci. Letters, 15 (1996) 1111-1114.*
"*Staphylococcus aureus*", http://en.wikipedia.org/wiki/Staphylococcus_aureus (Jun. 16, 2014).

* cited by examiner

*Primary Examiner* — Michael G Hartley
*Assistant Examiner* — Robert Cabral
(74) *Attorney, Agent, or Firm* — Johnson Legal, PLLC

(57) ABSTRACT

A liquid mixture that forms a film on a surface which inhibits the life functions of bacteria. In particular the film may include copper or silver, or a combination thereof, to provide an environment hostile to bacteria and other infectious organisms.

3 Claims, 1 Drawing Sheet

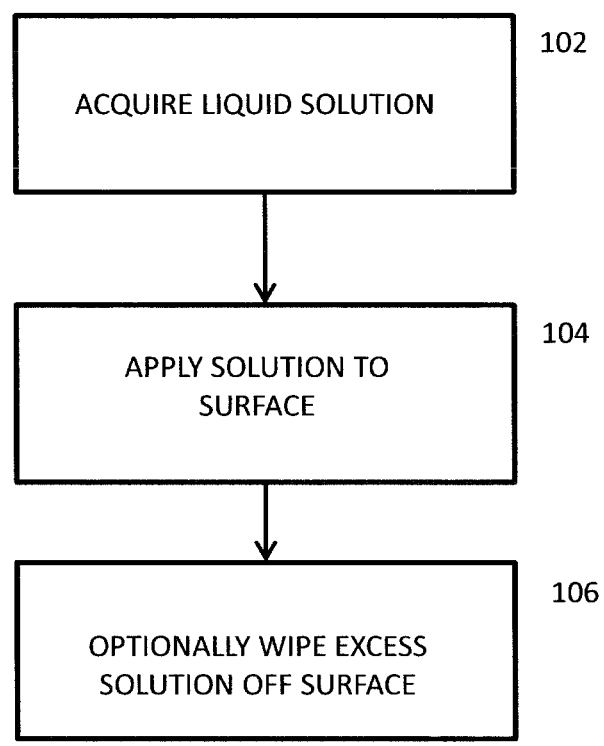

CLEANING AND SANITIZING FILM

RELATED APPLICATIONS

Priority is claimed to the provisional patent application Ser. No. 61/445,586 filed Feb. 23, 2011, the disclosure of which is incorporated by reference in its entirety.

FIELD OF THE INVENTION

The present invention relates generally to cleaners and, more particularly, to anti-bacterial cleaners.

BACKGROUND

Studies have shown that pure copper surfaces provide a more sanitary surface than stainless steel and other alloys. For example, MRSA, or Methicillin-resistant *Staphylococcus aureus*, can live for up to three days on surfaces such as stainless steel but was unable to survive on copper alloy surfaces for longer than 90 minutes. It is believed that the copper inhibits the bacteria's breathing and feeding and may even destroy its DNA.

MRSA is a resistant variation of the common bacterium *Staphylococcus aureus*. It has evolved an ability to survive treatment with beta-lactam antibiotics, including methicillin, dicloxacillin, nafcillin, and oxacillin. MRSA is especially troublesome in hospital-associated (nosocomial) infections. In hospitals, patients with open wounds, invasive devices, and weakened immune systems are at greater risk for infection than the general public. Hospital staff who do not follow proper sanitary procedures may transfer bacteria from patient to patient. Visitors to patients with MRSA infections or MRSA colonization are advised to follow hospital isolation protocol by using the provided gloves, gowns, and masks if indicated. Visitors who do not follow such protocols are capable of spreading the bacteria to cafeterias, bathrooms, and elevators.

Using copper or even copper alloys for different surfaces such as door handles, switch plates, etc. has a number of drawbacks. First of which is the expense. Secondly, copper and its alloys tend to readily oxidize which leads to an unsightly color as well as reduces the amount of copper available at the surface to fight any microbes. Coating the copper surface with a coating to inhibit oxidation will also reduce the copper's effectiveness at killing bacteria.

Accordingly, there is a need for an effective method of using copper (or a variety of other heavy metals) on surfaces to combat infections caused by bacteria, viruses and other microorganisms.

SUMMARY

Embodiments of the present invention relate to a solution that is used to clean any of a variety of surfaces that also leaves a film containing copper in order to provide a surface which can kill or inhibit the spread of bacteria such as MRSA and the like.

It is understood that other embodiments of the present invention will become readily apparent to those skilled in the art from the following detailed description, wherein it is shown and described only various embodiments of the invention by way of illustration. As will be realized, the invention is capable of other and different embodiments and its several details are capable of modification in various other respects, all without departing from the spirit and scope of the present invention. Accordingly, the drawings and detailed description are to be is regarded as illustrative in nature and not as restrictive.

BRIEF DESCRIPTION OF THE DRAWINGS

FIG. 1 depicts a flowchart of an exemplary method for cleaning surface in accordance with the principles of the present invention.

DETAILED DESCRIPTION

The detailed description set forth below is intended as a description of various embodiments of the invention and is not intended to represent the only embodiments in which the invention may be practiced. The detailed description includes specific details for the purpose of providing a thorough understanding of the invention. However, it will be apparent to those skilled in the art that the invention may be practiced without these specific details. In some instances, well known structures and components are shown in block diagram form in order to avoid obscuring the concepts of the invention.

Embodiments of the present invention relate to a mixture, beneficially a liquid mixture, that can be applied to a variety of different surfaces. In particular, the liquid includes copper and/or similar heavy metals in order to provide an environment that inhibits or kills infectious organisms such as, for example, MRSA. It is contemplated that the liquid mixture can be squirted on, aerosol sprayed on, poured on, brushed on, or wiped on a desired surface to be protected. Upon drying, the liquid mixture forms a relatively thin film that inhibits or kills infectious organisms that exist on the surface when applied or which are introduced to the surface during a time period after application. In addition to a liquid mixture, a powdered form is also contemplated that can be mixed with a solvent to form a liquid or slurry. The powdered form is similar to the liquid form in composition but with a majority of the water removed.

The proportions and amounts of different ingredients in the liquid mixture can be adjusted to have an effect on the thickness of the film that is formed. Film thicknesses from fractions of a millimeter to even smaller are contemplated. Thicker films may be used to offset wearing away in a high-traffic area. Additionally, the proportions and amounts of different ingredients can be adjusted to have an effect on how long the film will remain effective at fighting infectious organisms. For example, the amount of copper and other ingredients can be adjusted so that the film effectively kills microorganisms for a desired period of days, as well as physically remains in place, before needing to be re-applied. Additionally, the other ingredients may be adjusted or changed to form a film that is more stable or more wear-resistant depending on the intended application. Thus, a film that remains effective for a week or more is contemplated as well as a film that remains effective for a shorter period of time.

One example liquid mixture contemplated includes water, any of many well known chelating agents, copper or copper alloys, silver or silver alloys, one or more biocides, boric acid or similar acid, an amine compound, and a hexylamine compound. One of ordinary skill will recognize that functionally equivalent substitutions can be made for these ingredients without departing from the scope of the present invention. For example, other than copper and silver, some other heavy metals are also known to interfere with the feeding and breathing of various infectious microorganisms. Also, while the copper (or silver) may be in its substantially pure form, it can also be present in other chemical compounds that allow the copper (or silver) to effectively kill bacteria and the like such as MRSA. For example, copper sulfate or copper glutamate are non-pure forms of copper that can be used effectively.

In addition to a biocide, other compounds may be included such as, for example, fungicides, sporacides, and virucides to inhibit and kill other microorganisms in addition to bacteria. Because the liquid mixture can also be used as a cleaner and surface disinfectant, various detergents and other compounds may be added as well to augment those roles without departing from the scope of the present invention. One of ordinary skill will recognize that many alternative compounds and chemicals can be substituted to fulfill the following functions: the water acts as a solvent in which the other components are suspended, the chelating agent is useful for absorbing hard water salts; the copper and/or silver works as a biostatic component and short circuits bacteria's life functions; the biocide destroys the life function of bacteria; the boric acid functions as a biostatic component, corrosion inhibitor, and protective film; the amine compound provides alkalinity and combines with the boric acid to form a corrosion inhibitor and biostatic film that hold other components in place; and the hexylamine compound retards bacteria growth and acts as an anti-fungal agent.

In the table below are exemplary proportions of ingredients that form a mixture in accordance with embodiments of the present invention. The proportions, percentages by weight, are approximate and may be varied if additional ingredients are added or substituted:

| INGREDIENT | PROPORTION |
| --- | --- |
| Water | 60% to 90% |
| Chelating Agent | 0% to 10% |
| Copper | 1% to 20% |
| Silver | 0% to 5% |
| Biocide (fungicide, etc.) | .01% to 5% |
| Boric Acid | 0.1% to 10% |
| Amine Compound | 0.1% to 10% |
| Hexylamine Compound | 0.1% to 5% |

Thus, from the above table it can be seen that embodiments are contemplated that do not necessarily include a chelating agent and that there are embodiments contemplated that do not necessarily include silver. As mentioned earlier other components may be included to add detergency and cleaning ability to the mixture.

Additional ingredients, with exemplary percentages by weight, that can be included are:

| INGREDIENT | PROPORTION |
| --- | --- |
| Surfactant | 0.1% to 10% |
| Ammonium Chloride | 0.1% to 10% |
| Alcohol | 0.1% to 10% |
| Glycol Ether | 0.1% to 10% |
| Fragrance | 0.05 to 3.0% |
| Borates | 0.1% to 15% |

For example, Surfactants are usually organic compounds that are amphiphilic, meaning they contain both hydrophobic groups (their tails) and hydrophilic groups (their heads). Therefore, a surfactant molecule contains both a water insoluble (or oil soluble) component and a water soluble component. Surfactant molecules will typically diffuse in water and adsorb at interfaces between air and water or at the interface between oil and water, in the case where water is mixed with oil. The insoluble hydrophobic group may extend out of the bulk water phase, into the air or into the oil phase, while the water soluble head group remains in the water phase. This alignment of surfactant molecules at the surface modifies the surface properties of water at the water/air or water/oil interface.

The presence of an oxidizing agent provides beneficial results in inhibiting many type of bacteria and viruses. Thus addition of other compounds that improve the oxidizing nature of the film may be particularly beneficial. One example is hypochlorite, inclusion of this compound (e.g., at a proportion of about 10% or less by weight) in the film improves the film's ability to kill the most virulent strains of bacteria. Other solvents instead of, or in addition to, water may be used to improve the oxidizing nature of the film as well. Hydrogen peroxide, carbonated water, or similar solvents may be used to increase the amount of oxygen in the film available to inhibit bacteria and other infectious organisms. Also, embodiments are contemplated in which the water is distilled water.

One particular composition that provides beneficial results is described in the following table:

| INGREDIENT | PROPORTION |
| --- | --- |
| Water | 71.24% |
| Versene 220 (CAS#64-02-8) | 10.0% |
| Copper Sulfate (CAS#7758-98-7) | 3.5% |
| Dow Isopropanolamine mixture | 2.4% |
| Morpholine (CAS#110-91-8) | 0.5% |
| Fragrance AA08990 | 0.25% |
| Stepan BTC 2125M (EPA#1839-54) | 6.0% |
| Glycol Ether EB (CAS#11-76-2) | 3.0% |
| Biosoft N1-7 (CAS#34398-0101) | 0.5% |
| Isopropyl Alcohol (CAS#67-63-0) | 2.0% |
| Boric Acid (CAS#10043-35-3) | 0.6% |
| Sodium Troclosene (CAS#2893-78-9) | 0.01% |

In the above formula, particular percentages of components are provided by way of example. Other example percentages of components are contemplated within the scope of the present invention, even if not explicitly provided in the above table. The above percentages are approximate percentages and under standard manufacturing process can each vary by about ±5%. For some uses different ratios of ingredients can be used if the function of one ingredient is more appropriate than another for a given application. Also, the list of ingredients above identify a number of compounds by a particular product name or manufacturer name. However, where appropriate, a CAS number is also provided to more generically identify some of these compounds. In this disclosure, and in the claims below, a particular product name or manufacturer name is provided for clarity; however, providing such a name is not intended to limit the present invention to just these particular products but is intended to encompass the more generic compound underlying such a particular trade name. Also, for example, the Dow isapropanolamine mixture is a trio of compounds including about 12% MIPA, about 44% DIPA and about 44% TIPA. A similar mixture could be substituted without departing from the scope of the present invention.

Functional substitutes can be selected as well for some of the ingredient in the above table. For example, copper gluconate or substantially pure copper can be substituted, or used in addition to, the copper sulfate. A chelator other than Versene 220 can be selected as well. Different combinations of amines that act to buffer the solution's pH and enhance it stability can be used in addition to, or substituted for, the Isopropanolamine. Morpholine is known to break down cell walls, yet other similar compounds could be used as well. Isopropyl alcohol, Stepan, Glycol Ether, and Biosoft each provide varying degrees of cleaning ability and sterilization ability. Thus, variations in the percentages of these products could be used without departing from the scope of the present invention. Also, for example, as a substitute for the Sodium Troclosene, traizine could be used.

FIG. 1 depicts a flowchart of an exemplary method for cleaning surface in accordance with the principles of the present invention. In step 102 a liquid solution is acquired having a formulation identified in one of the above embodiments. Acquiring such a solution can involve mixing a number of relatively liquid ingredients to form a liquid solution but it can also involve formulating a dry, powdery mixture that is combined with water or another solvent to form a liquid solution. As used herein, "liquid solution" also includes a solution that has the consistency of a slurry. It is contemplated that the dry, powdery mixture of the ingredients could be useful in limited environments. Thus, such powder can be distributed over the surface of an object and provide similar protection and function as if the liquid solution is applied.

In step 104, the liquid solution is applied to a surface of one or more objects. It is contemplated that the liquid mixture can be squirted on, aerosol sprayed on, poured on, brushed on, or wiped on a desired surface to be protected. Upon drying, the liquid mixture forms a relatively thin film that inhibits or kills infectious organisms that exist on the surface when applied or which are introduced to the surface during a time period after application.

In step 106, there may be an optional step of wiping away excess solution from the surface of the object to which it is applied. The wiping step may also be useful for more evenly distributing the solution over the object's surface as well.

Embodiments of the present invention have particular use in hospitals or other medical-care environments. However, use of the invention is not limited to only these environments. For example, it can be used in any public area to help slow the spread of infections and sickness as well as used in a person's vehicle or home to provide a safer environment for anyone susceptible to infections. Recreational settings such as gyms and similar locations can benefit as well from embodiments of the present invention particularly where recreational equipment can be rented to or accessed by a number of different people.

Within any of these environments, the types of surfaces on which embodiments of the present invention can be applied are almost endless. Beneficial surfaces include doorknobs and switch plates because many different people are likely to touch those surfaces. Thus, the likelihood of infectious organisms being present is higher and the transference of these organisms to humans from these surfaces is higher as well. In addition, other surfaces include medical instruments, bed railings, table surfaces, shower and bath fixtures, and similar items. In general, any surface which is likely to come into contact with people or items that are transporting infectious organisms may be treated with embodiments of the present invention.

In addition to the surfaces mentioned above, prosthetics and other devices and objects that may be implanted within a body or that are frequently in contact with a portion of the body may be treated with embodiments of the present invention as well. For example, before an artificial knee is inserted or before a plastic surgery prosthetic is inserted in the body, their outer surface can be treated with embodiments of the present invention. Also, the medical or surgical devices involved in those types of procedures and other types of medical care can be treated with embodiments of the present invention as well.

An additional use of embodiments of the present invention is to apply the liquid mixture to filters that come in contact with air being circulated, or re-circulated, into a room. The filter could be part of a furnace or air conditioning system or a stand-alone air purifier system, or the like. In this application, the liquid mixture is applied in such a way that the air flow over or through the filter is not noticeably impeded The previous description is provided to enable any person skilled in the art to practice the various embodiments described herein. Various modifications to these embodiments will be readily apparent to those skilled in the art, and the generic principles defined herein may be applied to other embodiments. Thus, the claims are not intended to be limited to the embodiments shown herein, but are to be accorded the full scope consistent with each claim's language, wherein reference to an element in the singular is not intended to mean "one and only one" unless specifically so stated, but rather "one or more." All structural and functional equivalents to the elements of the various embodiments described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. §112, sixth paragraph, unless the element is expressly recited using the phrase "means for" or, in the case of a method claim, the element is recited using the phrase "step for."

What is claimed is:

1. A liquid mixture that forms an antimicrobial film when applied to a surface and allowed to dry, wherein the liquid mixture comprises:
    68%-74% by weight water;
    3.2%-3.8% by weight copper sulfate;
    2.2%-2.6% by weight isopropanolamine;
    0.4%-0.6% by weight morpholine; and
    0.5%-0.7% by weight boric acid,
wherein said boric acid and said isopropanolamine combine to form said antimicrobial film upon drying.

2. The liquid mixture of claim 1, wherein the liquid mixture further comprises:
    9.5%-10.5% by weight ethylenediaminetetraacetate (EDTA) salt;
    5.5%-6.5% by weight n-alkyl-dimethyl-benzyl-ammonium chloride and/or n-alkyl-dimethyl-ethylbenzyl-ammonium chloride;
    2.7%-3.3% by weight glycol ether;
    0.4%-0.6% by weight alcohol ethoxylate;
    1.8%-2.2% by weight isopropyl alcohol; and
    approximately 0.01% by weight sodium troclosene.

3. The liquid mixture of claim 1, wherein the isopropanolamine is one or more of: monoisopropanolamine (MIPA), diisopropanolamine (DIPA), and triisopropanolamine (TIPA).

* * * * *